United States Patent
Hauck et al.

[19]

[11] Patent Number: 6,096,218
[45] Date of Patent: *Aug. 1, 2000

[54] PROCESS FOR CONTROLLING THE PRESSURE IN A SIMULATED MOVING BED SEPARATION SYSTEM

[75] Inventors: Wilhelm Hauck, Nancy; Roger-Marc Nicoud, Richardmesnil, both of France

[73] Assignee: Institut Francais du Petrole, Cedex, France

[ * ] Notice: This patent issued on a continued prosecution application filed under 37 CFR 1.53(d), and is subject to the twenty year patent term provisions of 35 U.S.C. 154(a)(2).

[21] Appl. No.: 09/121,590

[22] Filed: Jul. 24, 1998

[30] Foreign Application Priority Data

Jul. 24, 1997 [FR] France .................................. 97/09548

[51] Int. Cl.$^7$ .................................................. B01D 15/08
[52] U.S. Cl. ........................................ 210/659; 210/198.2
[58] Field of Search .................................... 210/635, 656, 210/659, 662, 198.2

[56] References Cited

U.S. PATENT DOCUMENTS

| | | | |
|---|---|---|---|
| 3,268,605 | 8/1966 | Boyd .................................... | 210/662 |
| 3,291,726 | 12/1966 | Broughton .............................. | 208/310 |
| 4,599,115 | 7/1986 | Ando .................................... | 210/656 |
| 4,990,259 | 2/1991 | Kearney ................................. | 210/659 |
| 5,102,553 | 4/1992 | Kearney ................................. | 210/659 |
| 5,415,773 | 5/1995 | Noe ...................................... | 210/264 |
| 5,422,007 | 6/1995 | Nicoud .................................. | 210/659 |
| 5,595,665 | 1/1997 | Noe ...................................... | 210/662 |
| 5,653,072 | 8/1997 | Moran ................................... | 210/659 |
| 5,705,061 | 1/1998 | Moran ................................... | 210/198.2 |
| 5,762,806 | 6/1998 | Hotier .................................... | 210/659 |

FOREIGN PATENT DOCUMENTS

| | | | |
|---|---|---|---|
| 2550462 | 2/1985 | France ................................ | 210/198.2 |
| 8204265 | 12/1982 | WIPO ................................ | 210/198.2 |

*Primary Examiner*—Ernest G. Therkorn
*Attorney, Agent, or Firm*—Antonelli, Terry, Stout & Kraus, LLP

[57] ABSTRACT

Process for controlling the pressure in a separation system comprising a loop including several zones defined by fluid injection and fluid draw-off points is disclosed. A parameter such as the pressure is controlled at least at one point of the loop by acting on the global difference ($\delta$) between the flow rates of fluids injected and the flow rates of fluids drawn off by means of well-determined variations ($\delta_x$) applied to at least two injected and/or drawn off flows rates. This control is performed for example by imposing on each of these flow rates, variations ($\delta_x$) depending on the respective values of these flow rates, and for example variations proportional to the respective values (X) of these flow rates. It is for example possible to maintain one or two of the flow rates of fluids injected and drawn off constant. The process can be applied for separating aromatic hydrocarbons or optical isomers for example.

31 Claims, 1 Drawing Sheet

6,096,218

PROCESS FOR CONTROLLING THE PRESSURE IN A SIMULATED MOVING BED SEPARATION SYSTEM

BACKGROUND OF THE INVENTION

1. Field of the Invention

The present invention relates to a method for controlling the pressure prevailing in a simulated moving bed separation system through global control of the inlet/outlet flow rates.

2. Description of the Prior Art

Separation or fractionation processes based on (simulated moving bed) continuous chromatography are most often implemented in a device comprising a set of n chromatographic columns or column sections mounted in series (generally forming an open or a closed loop). A porous solid of well-determined grain size, distributed in different beds, constitutes the stationary phase.

Injection points intended for continuous injection of a solution referred to as feedstock, consisting of a mixture of compounds to be separated dissolved in a suitable fluid, and of an eluent, and fluid draw-off points are distributed along this loop. A flow referred to as raffinate (R), which contains the component that is the least readily retained by the stationary phase, is recovered downstream from a feedstock injection point. Another flow referred to as extract Ex, which contains the component that is the most readily retained by the stationary phase is recovered upstream from this feedstock injection point. An identical liquid flow passes through all the columns or column sections of the same zone. The raffinate flow rate is equal to the sum of the inlet flow rates minus the extract flow rate. In addition to these controlled flow rates, there is a recycle flow rate $Q_{Re}$. Several working zones are thus defined, each one defined by an injection and a draw-off point.

The injection and draw-off points are shifted at regular or non-regular time intervals in the direction of flow. The time interval between two injection/draw-off point shifts is referred to as at period.

Separation systems of this type are described for example in U.S. Pat. No. 2,985,589 and 4,402,832 and in pending U.S. Pat. application Ser. No. 09/097,590, filed by the assignee.

The inlet/outlet flow rates can take very different values according to the separations performed. It is well-known that the value of these flow rates (feedstock/extract for example) plays a significant part in the operation of the separation system.

The feedstock, eluent, extract and raffinate flow rates are denoted by $Q_{Feedstock}$, $Q_{El}$, $Q_{Ext}$, $Q_{Raf}$.

On an average in time, the sum (E) of the two inlet flow rates (feedstock and eluent) and the sum (S) of the two outlet flow rates (extract and raffinate) must be strictly identical, i.e.

$$E=S, \text{i.e. } Q_{Feedstock}+Q_{El}=Q_{Ext}+Q_{Raf}$$

To that effect, it is customary to control the flow rate of three of the four inlet/outlet flows of the system, the fourth one being controlled so as to maintain the pressure constant at a given point of the system. Such a technique is used and described for example in U.S. Pat. No. 3,291,726 and EP Pat. No. 0,586,385.

Selection of the pressure-controlled flow rate can be critical. In particular, if the flow rate selected is low, the relative variations of this flow rate, imposed by control, can be high in relation to the average value thereof, which may generate an unsatisfactory behavior likely to modify the inlet/outlet flow rate equilibrium. The pressure-controlled flow rate may therefore have to be changed according to the separations performed.

SUMMARY OF THE INVENTION

The process according to the invention allows to controlling of the pressure in a simulated moving bed component separation system comprising a loop including several zones defined by fluid injection points and fluid draw-off points. The process according to the invention finds applications notary in the control of aromatic hydrocarbon or optical isomer separation systems.

A parameter (the pressure for example) is controlled at least at one point of the loop by acting on the global difference ($\delta$) between the flow rates of fluids injected and the flow rates of fluids drawn off, by means of well-determined variations ($\delta_X$) applied to at least two flows injected and/or drawn off.

This control is performed for example by imposing, on each of these two flow rates, variations ($\delta_X$) depending on the respective values X of these flow rates.

According to an embodiment example, variations ($\delta_X$) proportional to the respective values X of these flow rates are imposed on each of these two flow rates.

According to another embodiment example at least one of the flows injected and drawn off is kept constant. It is also possible to maintain constant at least two flow rates among the flows injected and drawn off.

It is readily determined that the fluctuations of the flows injected and drawn off, resulting from the application of the process, are much better distributed and globally minimized in relation to conventional methods.

BRIEF DESCRIPTION OF THE DRAWINGS

Other features and advantages of the process according to the invention will be clear from reading the description hereafter of a non limitative example, with reference to the accompanying drawings wherein.

DETAILED DESCRIPTION OF THE INVENTION

Figure 1:
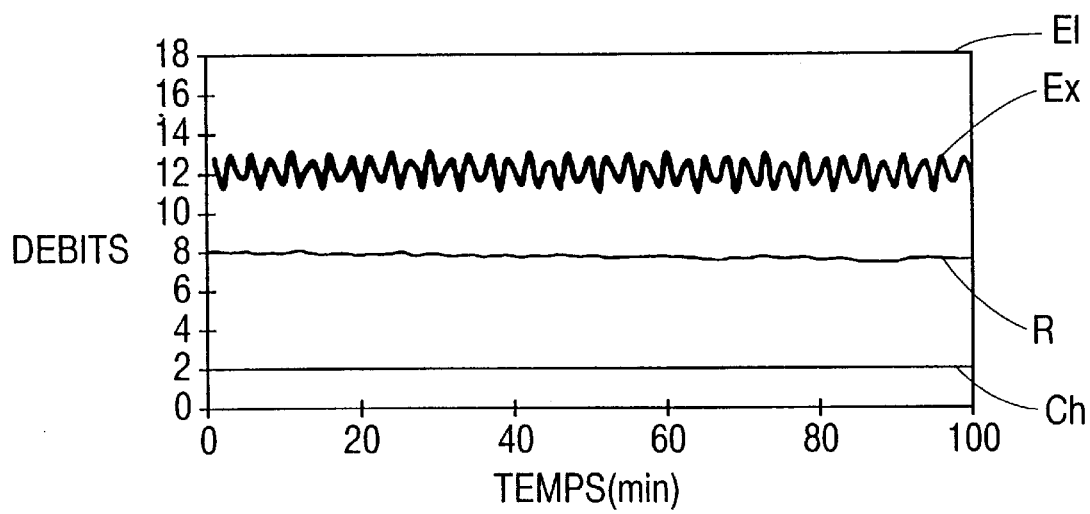
FIG. 1 shows the evolution of the feedstock (Ch), eluent (El), extract (Ex) and raffinate (R) flow rates in a loop where the pressure at the outlet of the last column is conventionally controlled by the extract flow rate.

The method of the invention, instead of controlling only one flow rate so as to maintain the pressure constant at a point of the loop, which results in an unsymmetrical system, exerts a global control in order to obtain the best possible distribution of the flow rate fluctuations throughout the system.

It is possible to regulate the pressure for example at a given point of the system by controlling the difference $\delta=(E-S)$ (which must be zero theoretically) between the sum of inlet flow rates E and the sum of outlet flow rate S. $\delta$ has to be decreased if the pressure increases in the system and it has to be increased if the pressure decreases. Pressure control by means of $\delta$ can for example be performed by a PID type algorithm.

The required value of $\delta$ being known, each of the inlet/outlet flow rates has to be determined and the flow rate fluctuations $\delta_X$ defined by:

$$Q_X^{real} = Q_X^{set} + \delta_X$$

have to be calculated, where subscript X can apply to the feedstock, to the eluent, to the extract or to the raffinate.

The equality $\delta_{Feedstock} + \delta_{Eluent} - \delta_{Extract} - \delta_{Raffinate} = \delta$ has of course to be satisfied.

In the usual implementation of the prior art, all the respective flow rate fluctuations $\delta_X$ of the fluids flows maintained at 0, except for one of them (the extract for example) which is therefore such that:

$$\delta_{Extract} = -\delta.$$

The best disturbance distribution sought is obtained by means of the method according to the invention by imposing that the fluctuations of at least two flow rates $\delta_X$ depend respectively on the flow rates X considered, with a general dependency relation of the following type:

$$\delta_X = f(X) \cdot \delta.$$

According to a particular non limitative example, a linear function f(X) can be selected, the proportionality factor depending on the flow rate value X and on at least one of the sum of or outlet in combined inlet flow rates E or S.

The following relation which connects $\delta_X$ to the absolute values X of the flow rates can for example be imposed:

$$\delta_x = \frac{X}{E+S} \cdot \delta$$

so that the disturbance is distributed porportionally to the value of the flow rates considered.

In some situations, one may have to maintain one or more flow rates strictly constant. If control of the inlet flow rates only is decided, $$\delta_x = \frac{X}{E} \cdot \delta$$

will be imposed for example, where subscript X denotes either the feedstock or the eluent, and $$\delta_X = 0,$$

subscript X denoting here either the extract or the raffinate.

If it has been decided to control the outlet flow rates only, $$\delta_x = \frac{X}{S} \cdot \delta$$

will be imposed for example, X denoting either the extract or the raffinate flow rate values, and $$\delta_X = 0,$$

x denoting either the feedstock or the eluent.

Comparative Example

Consider a separation system equipped with 10 2.5-cm diameter columns in which the various operating flow rates are as follows: recycle: 50 ml/min; feedstock: 2 ml/min; eluent: 18 ml/min; extract: 12 ml/min; raffinate: 8 ml/min.

At first, the pressure at the outlet of the last column is controlled by the extract flow rate (conventional system). In FIG. 1 which shows the evolution of the feedstock (Ch) eluent (El), extract (Ex) and raffinate (R) flow rates, it can be seen that the extract flow rate (Ex) exhibits relatively high fluctuations.

Figure 2:
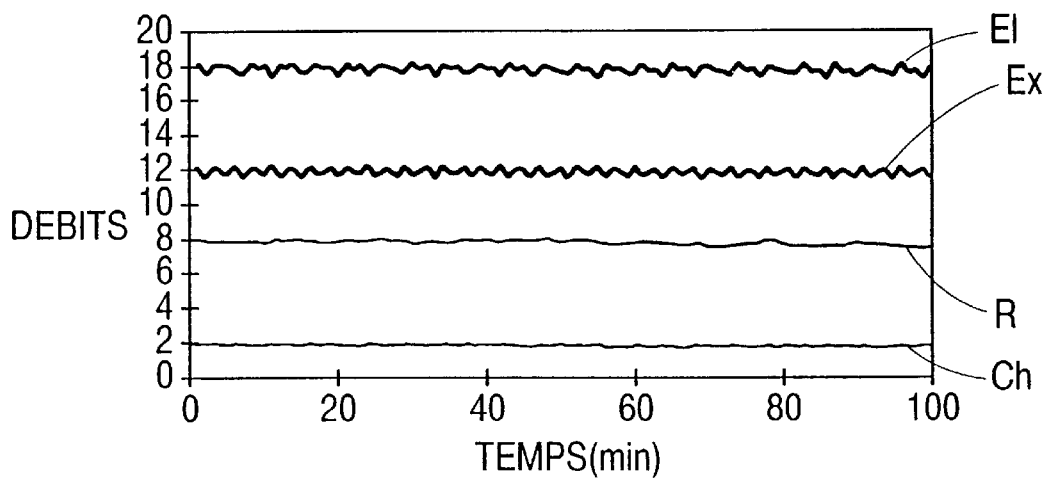
FIG. 2 shows the evolution of these flow rates by applying the method according to the invention.

Thereafter, the separation system is controlled in accordance with the method according to the invention by adjusting the four inlet/outlet flow rates. FIG. 2 shows that the fluctuations that occur for all the inlet/outlet flow rates are all low. The separation system therefore allows a better balanced operation.

What is claimed is:

1. A method of controlling a simulated moving bed operating in a controlled state including a loop with several zones defined by points of injection of fluids with injection flow rates and points of drawing off fluids with drawing off flow rates, comprising controlling one parameter in at least one of the points of the loop by acting on a difference ($\delta$) between the injection flow rates and the drawing off flow rates of the fluids by means of variations ($\delta_X$) applied to at least two injected and/or drawn off flows wherein:

$\delta = E - S$ where E is a sum of injected flow rates and S is a sum of drawing off flow rate and;

$\delta_X = Q_X^{real} - Q_X^{set}$ where $Q_X^{real}$ is a measurement of the injection flow rates or the drawing off flow rates and $Q_X^{set}$ is a set flow rate for the injection or drawing off flow rates.

2. A method as claimed in claim 1, wherein said parameter is pressure.

3. A method as claimed in claim 2, wherein the variations ($\delta_X$) are a function of respective values of each of the at least two flow rates of the injection and drawing off flow rates.

4. A method as claimed in claim 3, wherein the variations ($\delta_X$) are proportional to the values of each of the at least two flow rates of the injection and drawing off flow rates.

5. A method as claimed in claim 4, wherein at least one of the flow rates of the injected fluids and drawn off fluids is kept constant.

6. A method as claimed in claim 4, wherein at least two of the flow rates of the injected fluids and drawn off fluids is kept constant.

7. A method as claimed in claim 3, wherein at least one of the flow rates of the injected fluids and drawn off fluids is kept constant.

8. A method as claimed in claim 3, wherein at least two of the flow rates of the injected fluids and drawn off fluids is kept constant.

9. A method as claimed in claim 2, wherein the variations ($\delta_X$) are proportional to the values of each of the at least two flow rates of the injection and drawing off flow rates.

10. A method as claimed in claim 9, wherein at least one of the flow rates of the injected fluids and drawn off fluids is kept constant.

11. A method as claimed in claim 9, wherein at least two of the flow rates of the injected fluids and drawn off fluids is kept constant.

12. A method as claimed in claim 2, wherein at least two of the flow rates of the injected fluids and drawn off fluids is kept constant.

13. A method as claimed in claim 2, wherein at least one of the flow rates of the injected fluids and drawn off fluids is kept constant.

14. A method as claimed in claim 1, wherein the variations ($\delta_X$) are a function of respective values of each of the at least two flow rates of the injection and drawing off flow rates.

15. A method as claimed in claim 14, wherein the variations ($\delta_X$) are proportional to the values of each of the at least two flow rates of the injection and drawing off flow rates.

16. A method as claimed in claim 15, wherein at least one of the flow rates of the injected fluids and drawn off fluids is kept constant.

17. A method as claimed in claim 15, wherein at least two of the flow rates of the injected fluids and drawn off fluids is kept constant.

18. A method as claimed in claim 14, wherein at least one of the flow rates of the injected fluids and drawn off fluids is kept constant.

19. A method as claimed in claim 14, wherein at least two of the flow rates of the injected fluids and drawn off fluids is kept constant.

20. A method as claimed in claim 1, wherein the variations ($\delta_x$) are proportional to the values of each of the at least two flow rates of the injection and drawing off flow rates.

21. A method as claimed in claim 20, wherein at least one of the flow rates of the injected fluids and drawn off fluids is kept constant.

22. A method as claimed in claim 20, wherein at least two of the flow rates of the injected fluids and drawn off fluids is kept constant.

23. A method as claimed in claim 1, wherein at least one of the flow rates of the injected fluids and drawn off fluids is kept constant.

24. A method as claimed in claim 1, wherein at least two of the flow rates of the injected fluids and drawn off fluids is kept constant.

25. A method of controlling a simulated moving bed operating in a controlled state including a loop with several zones defined by points of injection of fluids with injection flow rates and points of drawing off fluids with drawing off flow rates, comprising controlling one parameter in at least one of the points of the loop by acting on a difference between the injection flow rates and the drawing off flow rates of the fluids by means of variations applied to at least two injected and/or drawn off flows.

26. A method as claimed in claim 25, wherein the variations are a function of respective values of each of the at least two flow rates of the injection and drawing off flow rates.

27. A method as claimed in claim 25, wherein said parameter is pressure.

28. A method as claimed in claim 27, wherein the variations are a function of respective values of each of the at least two flow rates of the injection and drawing off flow rates.

29. A method as claimed in claim 27, wherein the variations are proportional to the values of each of the at least two flow rates of the injection and drawing off flow rates.

30. A method as claimed in claim 27, wherein at least one of the flow rates of the injected fluids and drawn off fluids is kept constant.

31. A method as claimed in claim 27, wherein at least two of the flow rates of the injected fluids and drawn off fluids is kept constant.

* * * * *